(12) United States Patent
Adachi et al.

(10) Patent No.: US 8,275,454 B2
(45) Date of Patent: Sep. 25, 2012

(54) IONTOPHORESIS DEVICE ACTIVATED IN USE

(75) Inventors: Hirotoshi Adachi, Tsukuba (JP); Seiji Tokumoto, Tsukuba (JP); Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 1187 days.

(21) Appl. No.: 10/584,159

(22) PCT Filed: Dec. 27, 2004

(86) PCT No.: PCT/JP2004/019576
§ 371 (c)(1),
(2), (4) Date: Aug. 22, 2008

(87) PCT Pub. No.: WO2005/063331
PCT Pub. Date: Jul. 14, 2005

(65) Prior Publication Data
US 2011/0152743 A1 Jun. 23, 2011

(30) Foreign Application Priority Data
Dec. 26, 2003 (JP) .................. 2003-434854

(51) Int. Cl.
*A61N 1/30* (2006.01)
(52) U.S. Cl. ........................................ 604/20
(58) Field of Classification Search .......... 604/20; 424/443, 400, 447, 448
See application file for complete search history.

(56) References Cited

U.S. PATENT DOCUMENTS

| 4,474,570 | A | * | 10/1984 | Ariura et al. | 604/20 |
| 4,557,723 | A | * | 12/1985 | Sibalis | 604/20 |
| 4,622,031 | A | * | 11/1986 | Sibalis | 604/20 |
| 4,640,689 | A | * | 2/1987 | Sibalis | 604/20 |
| 4,842,577 | A | * | 6/1989 | Konno et al. | 604/20 |

(Continued)

FOREIGN PATENT DOCUMENTS

| EP | 0417290 A1 | 10/1989 |
| JP | 5-84180 B2 | 12/1993 |
| JP | 7-185016 A | 7/1995 |
| JP | 07-507464 A | 8/1995 |

(Continued)

*Primary Examiner* — Kevin C Sirmons
*Assistant Examiner* — Michael J Anderson
(74) *Attorney, Agent, or Firm* — Sughrue Mion, PLLC

(57) ABSTRACT

An iontophoresis device activated in use, which is capable of supplying a dissolution liquid in an amount that depends on the amount of a drug when it is used, is provided.

This iontophoresis device activated in use comprises: an absorber 11 formed of a material containing a dry drug 10 and capable of absorbing a liquid; a wall material 13 disposed around the absorber 11, having an adhesive layer 12 on the undersurface thereof; a support 15 disposed on the absorber 11 and the wall material 13, having an opening 14 in the central portion thereof; an electrode 25 disposed on the undersurface of the support 15; a diaphragm 20 disposed on the support 15; and a dissolution liquid reservoir 18 disposed on the diaphragm 20, retaining a dissolution liquid for dissolving the drug between the diaphragm 20 and itself, and having a protruding portion 17 for destroying the diaphragm 20 by pressing force. The protruding portion 17 has a linear apical portion, for example, and it is disposed so that it is allowed to come into contact with or is close to the diaphragm 20. A liner 19 is removably attached on the undersurface of both the absorber 11 and the adhesive layer 12.

12 Claims, 5 Drawing Sheets

U.S. PATENT DOCUMENTS

| | | | | |
|---|---|---|---|---|
| 5,288,289 | A | * | 2/1994 | Haak et al. ..................... 604/20 |
| 6,329,465 | B1 | * | 12/2001 | Takahashi et al. ............ 525/191 |
| 7,337,593 | B2 | * | 3/2008 | Blum et al. ..................... 53/453 |
| 2007/0264316 | A1 | * | 11/2007 | Adachi et al. ................ 424/448 |
| 2009/0221952 | A1 | * | 9/2009 | Tokumoto et al. ............. 604/20 |

FOREIGN PATENT DOCUMENTS

| | | |
|---|---|---|
| JP | 08-229140 A | 9/1996 |
| JP | 08-229140 A | 9/1996 |
| JP | 2-795466 B2 | 6/1998 |

* cited by examiner

IONTOPHORESIS DEVICE ACTIVATED IN USE

TECHNICAL FIELD

The present invention relates to an iontophoresis device, and in particular, to an iontophoresis device activated in use, to which a dissolution liquid is supplied to activate a drug, when it is used. This device is used as a device for delivering a bioactive substance into a living body using electric energy, or as a device for extracting a diagnostic substance from a living body to the outside.

BACKGROUND ART

Iontophoresis (e.g. Acta Dermatol venereol, vol. 64, p. 93, 1984) is a method of delivering a drug from the skin or mucosa using electric energy. In addition, there is also a method of extracting a diagnostic substance from a living body using the same principle, so as to observe the conditions of disease (e.g. Nature, Medicine, vol. 1, pp. 1198-120, 1995). In order to carry out these methods, an iontophoresis device having a desired structure is used as a device for delivering a bioactive substance, or as a device for extracting a diagnostic substance from a living body.

When an iontophoresis device that contains a chemically unstable drug is produced, it has been general to stabilize the drug by modifying the composition of its formulation. However, there are cases where such a drug cannot sufficiently be stabilized by devising the composition, because of the properties thereof. Thus, there has been proposed an iontophoresis device, wherein such a drug is conserved in a dry state and a liquid is then supplied to the dry drug when it is used.

For example, Patent Document 1 discloses an interface used for iontophoresis. In the case of this interface, a dry drug particle-adhered surface has been formed on one surface of a porous body, and when it is used, such a drug particle-adhered surface is allowed to come into contact with the skin of a living body. A hollow needle provided on a reservoir that contains a carrier solution is inserted into the reservoir from the top of a supporting member, so that they can be communicated with each other. Thus, the carrier solution is supplied to a porous body via the hollow needle and a conductive member. Thereafter, the conductive member is energized. The carrier solution permeates into the conductive member and the porous body, and it then reaches the drug particle-adhered surface. Thereafter, the carrier solution is mixed with the drug particle-adhered surface, so that they become a liquid. A liquid drug layer is formed on the skin surface of the living body, and the drug further permeates into the living body by electric force.

Patent Document 1: Japanese Patent No. 2795466

Patent Document 2 discloses a novel plaster structure used for iontophoresis. As shown in FIG. 4, this structure has such a structure that a capsule containing an electrolyte solution is provided in the upper portion of the plaster structure, and that a thin film such as an aluminum foil provided between the capsule and a water-containing layer is then destroyed when it is attached, thereby allowing the electrolyte solution to permeate therein, for example. When a water-degradable drug is used, it is said that it is adequate to provide a plaster structure, wherein a drug-containing layer and a water-containing layer are controlled in a dry state and which comprises a capsule containing an electrolyte solution.

Patent Document 2: Japanese Patent Publication No. 5-84180

Disclosure of the Invention

Problems to be Solved by the Invention

When a drug is conserved in a dry state and a liquid is supplied to such a dry drug when it is used in the aforementioned iontophoresis device, such a liquid must be supplied in an amount that depends on the amount of the drug. However, with regard to the aforementioned prior art techniques, the detailed structure of a reservoir or capsule that contains a carrier solution or electrolyte solution has not been clarified. There is a risk that a carrier solution or electrolyte solution remains in a reservoir or capsule after the use of these devices, and there is also a risk that a liquid cannot be supplied in an amount that depends on the amount of a drug.

Accordingly, it is an object of the present invention to provide an iontophoresis device activated in use (electrode structure), which is able to supply a dissolution liquid in an amount that depends on the amount of a drug, when it is used.

Means for Solving the Problems

The aforementioned object of the present invention is achieved by an iontophoresis device activated in use, which comprises: an absorber formed of a material containing a dry drug and capable of absorbing a liquid; a wall material disposed around the above described absorber, having an adhesive layer on the undersurface thereof; a support disposed on the above described absorber and the above described wall material, having an opening in the central portion thereof; an electrode disposed on the undersurface of the above described support; a diaphragm disposed on the above described support; and a dissolution liquid reservoir disposed on the above described diaphragm, retaining a dissolution liquid for dissolving the above described drug between the above described diaphragm and itself, and having a protruding portion for destroying the above described diaphragm by pressing force. Herein, the above iontophoresis device activated in use may also comprise a solution permeable film on the undersurface of the above described absorber, and further, it may also comprise a liner on the undersurface of both the above described absorber and the above described adhesive layer, wherein the liner has a concave portion opposed to the above described absorber.

In addition, the iontophoresis device activated in use of the present invention comprises: a drug-containing layer containing a dry drug; an absorber disposed on the above described drug-containing layer and formed of a material capable of absorbing a liquid; a wall material disposed around the above described absorber, having an adhesive layer on the undersurface thereof; a support disposed on the above described absorber and the above described wall material, having an opening in the central portion thereof; an electrode disposed on the undersurface of the above described support; a diaphragm disposed on the above described support; and a dissolution liquid reservoir disposed on the above described diaphragm, retaining a dissolution liquid for dissolving the above described drug between the above described diaphragm and itself, and having a protruding portion for destroying the above described diaphragm by pressing force. Herein, the above iontophoresis device activated in use may also comprise a liner on the undersurface of both the above described drug-containing layer and the above described adhesive layer, wherein the liner has a concave portion opposed to the above described drug-containing layer.

Moreover, the iontophoresis device activated in use of the present invention comprises: a support; an electrode disposed on the upper surface of the above described support; an absorber disposed on the above described support and the above described electrode and formed of a material containing a dry drug and capable of absorbing a liquid; a wall material disposed around the above described absorber on the above described support, having an adhesive layer on the upper surface thereof; a liner disposed on the above described absorber and the above described adhesive layer, having an opening in the central portion thereof; a diaphragm disposed on the above described liner; and a dissolution liquid reservoir disposed on the above described diaphragm, retaining a dissolution liquid for dissolving the above described drug between the above described diaphragm and itself, and having a protruding portion for destroying the above described diaphragm by pressing force. Herein, the above iontophoresis device activated in use may also comprise a solution permeable film on the upper surface of the above described absorber.

Furthermore, the iontophoresis device activated in use of the present invention comprises: a support; an electrode disposed on the upper surface of the above described support; an absorber disposed on the above described support and the above described electrode and formed of a material capable of absorbing a liquid; a wall material disposed around the above described absorber on the above described support, having an adhesive layer on the upper surface thereof; a drug-containing layer disposed on the above described absorber and containing a dry drug; a liner disposed on the above described drug-containing layer and the above described adhesive layer, having an opening in the central portion thereof; a diaphragm disposed on the above described liner; and a dissolution liquid reservoir disposed on the above described diaphragm, retaining a dissolution liquid for dissolving the above described drug between the above described diaphragm and itself, and having a protruding portion for destroying the above described diaphragm by pressing force.

Herein, the dissolution liquid-contacting portion of the above described diaphragm has an oval form, and the protruding portion of the above described dissolution liquid reservoir may have a linear apical portion that extends in the longitudinal direction of the above described oval form. In this case, assuming that the length of the above described linear apical portion is given by L1 and the length of the dissolution liquid-contacting portion of the above described diaphragm in the longitudinal direction is given by L2, it is preferable to satisfy such a relationship as $0.1 \times L2 \leq L1 \leq 0.5 \times L2$. In addition, the dissolution liquid-contacting portion of the above described diaphragm has a round form, and the protruding portion of the above described dissolution liquid reservoir may have cross-shape apical portions. In this case, assuming that the lengths of the above described cross-shape apical portions are given by L10 and L11 and the diameter of the dissolution liquid-contacting portion of the above described diaphragm is given by L2, it is preferable to satisfy such relationships as $0.1 \times L2 \leq L10 \leq 0.5 \times L2$ and/or $0.1 \times L2 \leq L11 \leq 0.5 \times L2$.

Furthermore, it is preferable that the peripheral portion of the opening of the above described support be dented to the above described absorber side, rather than other portions. Still further, it is preferable that the above described support be inclined so that the opening is closer toward the above described absorber side than the peripheral portion of the support. Similarly, it is preferable that the peripheral portion of the opening of the above described liner be dented to the above described absorber side more than the rest of the liner. Still further, it is preferable that the peripheral portion the above described liner be inclined so that the opening is closer toward the above described absorber side than the peripheral portion of the liner.

Still further, it is preferable that the above described dissolution liquid reservoir be formed by processing of a sheet material, and that the above described sheet material have a water vapor permeability of 0.22 $g/m^2 \cdot 24$ hr or less. Still further, the above described sheet material preferably has a thickness between approximately 250 and approximately 350 μm. For example, the above described sheet material may comprise a cyclic polyolefin copolymer film, and it is preferably a laminated film consisting of a cyclic polyolefin copolymer film and a polyolefin film. Further, the above described sheet material may comprise a fluorocarbon resin film, and it is preferably a laminated film consisting of a fluorocarbon resin film and a polyolefin film. Further, the above described diaphragm may be an aluminum foil.

Advantages of the Invention

The present invention provides an iontophoresis device activated in use, which is able to supply a dissolution liquid in an amount that depends on the amount of a drug when it is used. In addition, since this device enables a reduction in the amount of a liquid remaining in a dissolution liquid reservoir, a drug can be evenly activated. By supplying a dissolution liquid according to the present invention, the concentration of a drug becomes almost uniform in various sites. Moreover, it becomes possible to rapidly supply a dissolution liquid contained in the dissolution liquid reservoir, when it is used.

Figure 1:
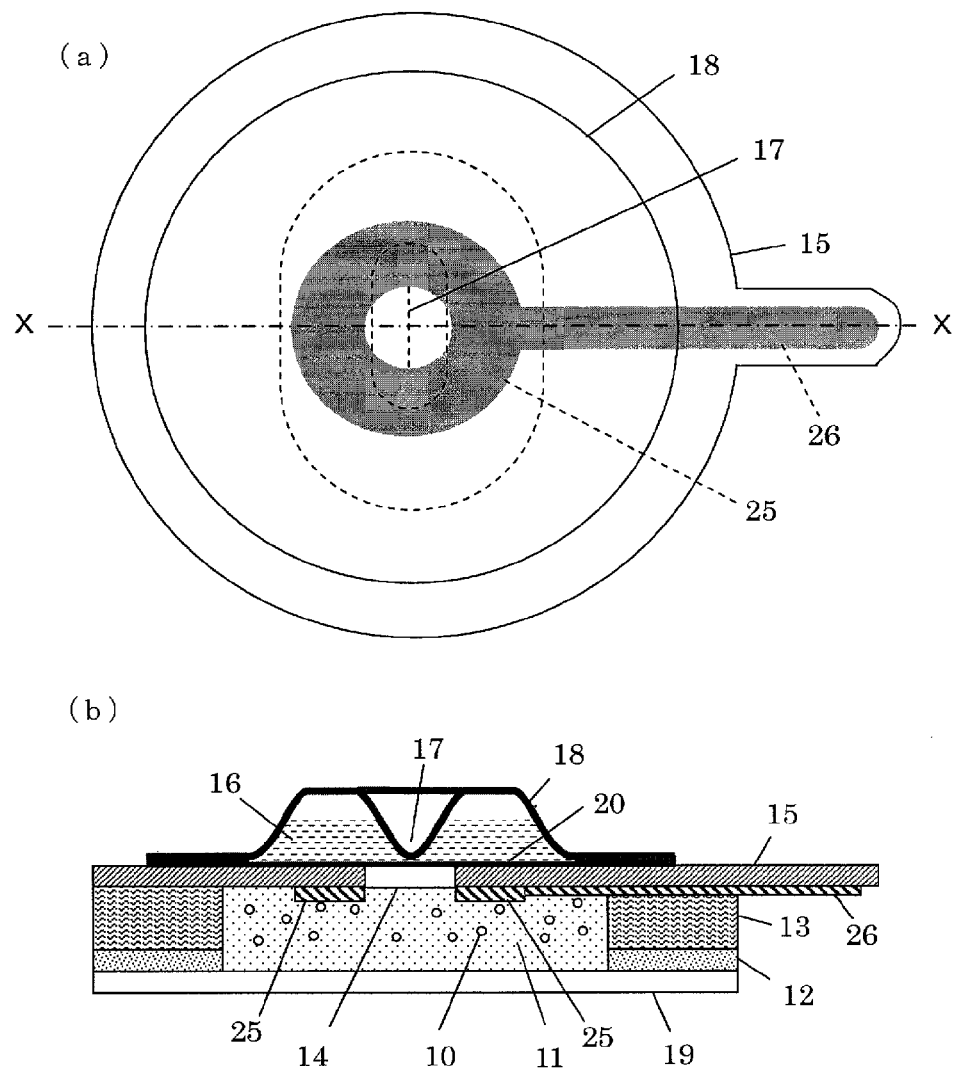
FIG. 1 is a view showing a structure example of the iontophoresis device activated in use of the present invention, wherein (a) represents a plan view, and (b) represents a cross-sectional view of (a) along the line X-X.

DESCRIPTION OF SYMBOLS 10, 40 Drug
11, 41 Absorber containing a dry drug
12, 42 Adhesive layer
13, 43 Wall material
14, 44 Opening
15, 45 Support
16, 46, 91 Dissolution liquid
17, 47, 94 Protruding portion
18, 48, 90 Dissolution liquid reservoir
19, 49, 79, 89 Liner
20, 50, 92 Diaphragm
21, 51 Solution permeable film
25, 55 Electrode
26, 56 Lead portion
31, 61 Absorber containing no drug
32, 62 Drug containing layer

BEST MODE FOR CARRYING OUT THE INVENTION

FIG. 1 is a view showing a structure example of the iontophoresis device activated in use of the present invention, wherein (a) represents a plan view, and (b) represents a cross-sectional view of (a) along the line X-X. As shown in the figure, the device of the present example comprises: an absorber 11, which is formed of a material containing a dry drug 10 and capable of absorbing a liquid; a wall material 13, which is disposed around the absorber 11 and has an adhesive layer 12 on the undersurface thereof; a support 15, which is disposed on the absorber 11 and the wall material 13 and has an opening 14 in the central portion thereof; an electrode 25 disposed on the undersurface of the support 15; a diaphragm 20 disposed on the support 15; and a dissolution liquid reservoir 18, which is disposed on the diaphragm 20, retains a dissolution liquid for dissolving the drug between the diaphragm 20 and itself, and has a protruding portion 17 for destroying the diaphragm 20 by pressing force. As shown in the figure, the protruding portion 17 has a linear apical portion, for example, and it is disposed such that it is allowed to come into contact with or is close to the diaphragm 20. A liner 19 is removably attached on the undersurface of both the absorber 11 and the adhesive layer 12. Herein, the dissolution liquid reservoir 18 and the diaphragm 20 may be formed, either separately or integrally. The dissolution liquid reservoir 18 is combined with the diaphragm 20, so as to form a dissolution liquid container Moreover, the shape of the opening 14 of the support is not particularly limited. Any shape can be adopted, as long as it is a shape capable of evenly supplying a solution to the absorber 11. It is preferably a round shape, for example. In this case, the size of the opening 14 depends on the size of the absorber 11. For example, the above opening 14 has a diameter between 2 mm and 10 mm, and preferably between 4 mm and 8 mm. It is also possible that the support 15 be omitted, and that the diaphragm 20 be allowed to have the functions of the support 15. In this case, an opening has not been provided, but such an opening is formed by a protruding portion when it is used.

The electrode 25 and a lead portion 26 are produced by printing on the undersurface of the support 15, for example. The electrode 25 is connected with one output terminal (for example, positive electrode) of a power supply, which is not shown in the figure, via the lead portion 26. The other output terminal (for example, negative electrode) of the power supply is connected with a counter device, which is not shown in the figure. The structure of the counter device can be the same as that of the present iontophoresis device. However, it is not always necessary that it contain a drug. An electric voltage or current used for iontophoresis is supplied from the power supply to a portion between the present iontophoresis device and the counter device.

When the present iontophoresis device is used, first, the upper portion of the dissolution liquid reservoir 18 or protruding portion 17 is pressed, so that the protruding portion 17 breaks the diaphragm 20. At this time, the diaphragm 20 is largely broken along the linear apical portion of the protruding portion 17, and a dissolution liquid contained in the dissolution liquid reservoir 18 is supplied to the absorber 11 via the opening 14 of the support 15. The absorber 11 gets wet with this dissolution liquid, and the drug 10 is evenly activated. Thereafter, the liner 19 is removed, and the present device is attached to the skin. By actuating a power supply used for iontophoresis, an electric voltage or current is supplied to a portion between the present iontophoresis device and the counter device. Thereby, the activated drug permeates into the skin. In the present example, the dissolution liquid reservoir 18 remains attached to the main body of the device. Thus, it is not necessary to wait for attachment, until the dissolution liquid contained in the dissolution liquid reservoir 18 gets empty. This is because even if a dissolution liquid remains in the dissolution liquid reservoir 18 when the device is used, it is gradually supplied to the absorber 11.

The following components can be used in each portion of the iontophoresis device of the present invention.

As a drug, various types of drugs can be selected depending on therapeutic purpose. The present device is particularly useful for the use of a drug whose tolerance dose is rigidly determined, when the drug is administered using iontophoresis. For example, the present device can be used safely for a drug having a narrow width between the effective blood level and the concentration necessary for the expression of side effects, such as insulin. Moreover, even in the case of other drugs having a relatively broad width between the effective blood level and the concentration necessary for the expression of side effects, in order to obtain the high safety and effectiveness of the drugs, it is important to suppress electrical error factors to the minimum.

With regard to the drug (active ingredient) used in the present invention, the type of the drug, the type of the salt thereof, the application of the drug, and the like, are not particularly limited, as long as it is a compound having a pharmacological activity. Examples of such a drug used in the present invention may include an antibiotic, an antifungal drug, an antitumor drug, a cardiac stimulant, an antiarrhythmic drug, a vasodilator, an antihypertensive drug, a diuretic, a hypotensive diuretic, a cardio vascular drug, an anti-platelet drug, a hemostatic, an antihyper lipidemic drug, an antipyretic, analgesic, and antiphlogistic drug, an antirheumatic drug, a relaxant, an antitussive expectorant drug, an antiulcer drug, a sedative, an antiepileptic drug, an antidepressive drug, an antiallergic drug, an antidiabetic drug, an antituberculous drug, a hormone drug, a narcotic antagonist, an osteoclastic inhibitor, an antiangiogenic drug, and a local anesthetic. A preferred usage pattern of the present device is a hydrochloride of an active ingredient. In addition, the type and number of an active ingredient contained in each electrode structure are not particularly limited. In order to enhance pharmacological effects, it may also be possible that different types of active ingredients be contained in each electrode structure. In a more preferred embodiment, at least one type of active ingredient is contained in two devices (electrode structures).

Examples of an antibiotic used here in may include gentamicin sulfate, lipidomycin, sisomicin sulfate, tetracycline hydrochloride, ampicillin, cefalotin sodium, cefotiam dihydrochloride, cefazolin sodium, thienamycin, sulfazecin, streptomycin sulfate, kanamycin sulfate, rifampicin, vancomycin hydrochloride, ofloxacin, and cefoselis sulfate.

Examples of an antifungal drug used herein may include amphotericin B, itraconazole, fluconazole, miconazole, and 2-[(1R,2R)-2-(2,4-difluorophenyl-2-hydroxy-1-methyl-3-(1H-1,2,4-triazol-1-yl)propyl)-4-[4-2,2,3,3-tetrafluoropropoxy]phenyl]-3(2H, 4H)-1,2,4-triazolone.

Examples of an antitumor drug used herein may include bleomycin hydrochloride, tegafur, actinomycin D, mitomycin C, adriamycin, fluorouracil, 6-mercaptopurine, cytarabine, procarbazine, doxorubicin hydrochloride, methotrexate, and tamoxifen citrate.

Examples of an antituberculous drug used herein may include streptomycinsulfate, kanamycinsulfate, isoniazid, ethambutol hydrochloride, and pyrazinamide.

Examples of a cardiac stimulant used herein may include transbioxo camphor, teofilol, dopamine hydrochloride, dobutamine hydrochloride, and ubidecarenone.

Examples of an antiarrhythmic drug used herein may include propranolol hydrochloride, oxyprenol hydrochloride, procainamide hydrochloride, lidocaine, phenytoin, metoprolol tartrate, verapamil hydrochloride, and diltiazem hydrochloride.

Examples of a vasodilator used herein may include oxyfedrine hydrochloride, tolazoline hydrochloride, pametan sulfate, nicardipine hydrochloride, verapamil hydrochloride, and papaverine hydrochloride.

Examples of an antihypertensive drug used herein may include hydralazine hydrochloride, budralazine, prazosin hydrochloride, doxazosin mesilate, carteolol hydrochloride, clonidine hydrochloride, enalapril maleate, captopril, delapril hydrochloride, manidipine hydrochloride, pinacidil, minoxidil, losartan, candesartan cilexetil, valsartan, telmisartan, and irbesartan.

Examples of a diuretic used herein may include acetazolamide, methazolamide, chlorothiazide, furosemide, triamterene, amiloride, and aminometradine.

Examples of a hypotensive diuretic used herein may include pentolinium and hexamethonium bromide.

Examples of a cardiovascular drug used herein may include alprostadil, limaprost, ozagrelsodium, clopidogrelbisulfate, beraprost, ciprostene, iloprost, ataprost, clinprost, ethyl icosapentate, etilefrine hydrochloride, dihydroergotamine mesylate, pamicogrel, tranilast, probucol, candesartan cilexetil, sodium citrate, DX-9065a, heparin, low molecular weight heparin, nifedipine, efonidipine hydrochloride, diltiazem hydrochloride, and tranilast.

Examples of an anti-platelet drug used herein may include ticlopidine, satigrel, limaprost alfadex, clinprost, clopidogrel bisulfate, sibrafiban, eptibatide, tirofiban hydrochloride, sarpogrelate hydrochloride, zemilofiban hydrochloride, orbofiban acetate, isbogrel, cilostazol, aspirin, abximab, and (S)-4-(4-guanidinobenzoylamino)acetyl-3-[3-(4-guanidinobenzoylamino)]propyl-2-oxopiperazin-1-acetic acid or a salt thereof.

Examples of a hemostatic used herein may include epinephrine, menadione sodium bisulfite, acetomenaphthone, and tranexamic acid.

Examples of an antihyperlipidemic drug used herein may include pravastatin sodium, simvastatin, fluvastatin sodium, serivastatin, and atorvastatin.

Examples of an antipyretic, analgesic, and antiphlogistic drug used herein may include aspirin, sodium salicylate, sulpyrine, indomethacin, diclofenacsodium, loxoprofensodium, ferbinac, zaltoprofen, piroxicam, nimesulide, meloxicam, celexicob, tialamide, emorfazone, buprenorphine, eptazocine hydrobromide, pentazocine, butorphanol tartrate, tramadol hydrochloride, ketorolac, meperidine hydrochloride, morphine hydrochloride, morphine sulfate, hydromorphine, fentanyl citrate, fentanyl, and mofezolac.

Examples of an antirheumatic drug used herein may include methotrexatehydrochloride, goldsodiumthiomalate, auranofin, bucillamine, D-penicillamine, actarit, lobenzarit, mizoribine, salazosulfapyridine, and tacrolimus hydrate.

Examples of a muscle relaxant used herein may include pridinol methanesulfonate, tubocurarine hydrochloride, eperisone hydrochloride, tizanidine hydrochloride, chlorphenesin carbamate, tolperisone hydrochloride, dantrolene sodium, baclofen, and lanperisone hydrochloride.

Examples of an antitussive expectorant drug used herein may include ephedrine hydrochloride, codeine'phosphate, picoperidamine hydrochloride, ambroxol, bromhexine hydrochloride, salbutamolsulfate, tulobuterolhydrochloride, formoterol fumarate, azelastine hydrochloride, ketotifen fumarate, and picoperidamine.

Examples of an antiulcer drug used herein may include ornoprostil, cimetidine, famotidine, ranitidinehydrochloride, metoclopramide, omeprazole, and lansoprazole.

Examples of a sedative used herein may include chlorpromazine hydrochloride, atropine sulfate, and fluphenazine enanthate.

Examples of an antiepileptic drug used herein may include phenytoin sodium and ethosuximide.

Examples of an antidepressive drug used herein may include amitriptyline hydrochloride, imipramine hydrochloride, clomipramine hydrochloride, desipramine hydrochloride, maprotiline hydrochloride, and phenelzine sulfate.

Examples of an antiallergic drug used herein may include diphenylhydramine hydrochloride, tripelennamine hydrochloride, clemizole hydrochloride, chlorpheniramine d-maleate, cyproheptadine hydrochloride, ketotifenfumarate, epinastine, and tacrolimus hydrate.

Examples of an antidiabetic drug used herein may include glymidine sodium, glipizide, metformin, tolbutamide, chlorpropamide, glibenclamide, acetohexamide, midaglizole, glimepiride, senaglinide, repaglinide, and pioglitazone hydrochloride.

Examples of an antituberculous drug used herein may include streptomycinsulfate, kanamycinsulfate, isoniazid, ethambutol hydrochloride, and pyrazinamide.

Examples of a hormone drug used herein may include β-estradiol, testosterone enanthate, prednisolone succinate, dexamethasone sodium phosphate, and methimazole.

Examples of a narcotic antagonist used herein may include levallorphan tartrate, nalorphine hydrochloride, protamine, and naloxone.

Examples of an osteoclastic inhibitor used herein may include (sulfur-containing alkyl)aminomethylenebisphosphonic acid, raloxifene, sodium alendronate, disodium incadronate, tibolone, cimadronate, risedronate, disodiumclodronate, falecalcitriol, calcitriol, alfacalcitriol, didronel sodium, ipriflavone, and minodronic acid.

Examples of an antiangiogenic drug used herein may include a vascularization inhibitory steroid [refer to Science, vol. 221, p. 719 (1983)], and a fumagilol derivative [refer to O-monochloroacetyl carbamoyl fumagilol, O-dichloroacetyl carbamoyl fumagilol, etc., (EP Patent Nos. 357061, 359036; 386667, and 415294)].

Examples of a local anesthetic used herein may include lidocaine hydrochloride, tetracaine hydrochloride, procaine hydrochloride, benzocaine hydrochloride, etidocaine hydrochloride, prilocaine hydrochloride, dibucaine hydrochloride, bupivacaine hydrochloride, cocaine hydrochloride, ethylaminobenzoate, orthocainehydrochloride, oxethazaine hydrochloride, and mepivacaine hydrochloride.

Examples of other active ingredients may include a peptide, a protein, and a compound having pharmacologic activity such as nucleic acid or oligosaccharide.

When an amino acid, a peptide, and the like are expressed with abbreviated symbols, such abbreviated symbols are based on the abbreviated symbols in accordance with IUPAC-IUB Commission on Biochemical Nomenclature, or abbreviated symbols commonly used in the present field. In addition, when an amino acid has an optical isomer, it represents an L-form, unless otherwise specified.

The following peptides are used:

A derivative having the same action as that of a luteinizing hormone-releasing hormone (LH-RH), LH-RH, for example, a polypeptide represented by the following formula (I) or a salt thereof:

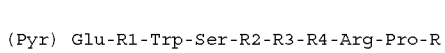

(Pyr) Glu-R1-Trp-Ser-R2-R3-R4-Arg-Pro-R    (I)

[wherein R1 represents His, Tyr, Trp, orp-NH2-Phe; R2 represents Tyr or Phe; R3 represents Gly or a D-type amino acid residue; R4 represents Leu, Ile, or Nle; and R5 represents Gly-NH—R6 (wherein R6 represents H or a lower alkyl group that may have a hydroxyl group) or NH—R6 (wherein R6 have the same definitions as described above)] [refer to U.S. Pat. Nos. 3,853,837, 4,008,209 and 3,972,859, G.B. Patent No. 1423083, Proceedings of the National Academy of Science, vol. 78, pp. 6509-6512 (1981)].

An LH-RH antagonist, for example, a polypeptide represented by the following formula (II) or a salt thereof:

N-α-t-butoxycarbonyl-O-benzyl-Ser-Trp-Ser-Tyr-Xl-
Leu-Arg-Pro-GlyNH2    (II)

[wherein Xl represents D-Ser or D-Trp] (refer to U.S. Pat. Nos. 4,086,219, 4,124,577, 4,253,997, and 4,317,815).

Insulin, somatostatin, or a somatostatin derivative, for example, a polypeptide represented by the following formula (III) or a salt thereof:

(III)

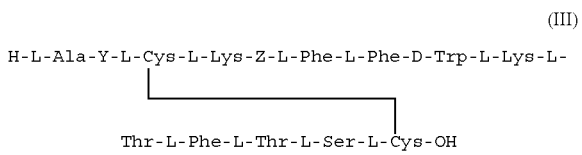

H-L-Ala-Y-L-Cys-L-Lys-Z-L-Phe-L-Phe-D-Trp-L-Lys-L-
Thr-L-Phe-L-Thr-L-Ser-L-Cys-OH

[wherein Y represents D-Ala, D-Ser, or D-Val; and Z represents Asn or Ala] (refer to U.S. Pat. Nos. 4,087,390, 4,093,574, 4,100,117, and 4,253,998).

An adrenocorticotropic hormone (ACTH); a melanocyte-stimulating hormone (MSH); a thyroid stimulating hormone releasing hormone (TRH); and a derivative thereof, for example, a compound represented by the following formula (IV) or a salt thereof:

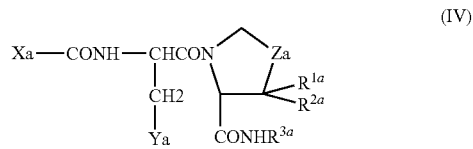

(IV)

[wherein Xa represents a 4-, 5-, or 6-membered heterocyclic group; Ya represents imidazol-4-yl or 4-hydroxyphenyl; Za represents CH2 or S; each of $R^{1a}$ and $R^{2a}$ identically or differently represents hydrogen or a lower alkyl group; and $R^{3a}$ represents hydrogen or an aralkyl group that may have a substituent] (refer to Japanese Patent Laid-Open Nos. 50-121273 and 52-116465).

A parathyroid hormone (PTH) or a derivative thereof, for example, a peptide represented by the following formula (V) or a salt thereof:

(V)

R1'-Val-Ser-Glu-Leu-R2'-His-Asn-R3'-R4'-R5'-His-
Leu-Asn-Ser-R6'-R7'-Arg-R8'-Glu-R9'-Leu-R10'-
R11'-R12'-Leu-Gln-Asp-Val-His-Asn-R13'

[wherein R1' represents Ser or Aib; R2' represents Met or a natural fat-soluble amino acid; R3' represents Leu, Ser, Lys, or an aromatic amino acid; R4' represents Gly or a D-amino acid; R5' represents Lys or Leu; R6' represents Met or a natural fat-soluble amino acid; R7' represents Glu or a basic amino acid; R8' represents Val or a basic amino acid; R9' represents Trp or 2-(1,3-dithiolan-2-yl)Trp; R10' represents Arg or His; R11' represents Lys or His; R12' represents Lys, Gln, or Leu; and R13' represents Phe or Phe-NH2] (refer to Japanese Patent Laid-Open Nos. 5-32696 and 4-247034, and European Patent Laid-Open Nos. 510662, 477885 and 539491); a peptide fragment at the N-terminus (positions 1-34) of human PTH (hereinafter abbreviated as hPTH (1→34)) [refer to G. W. Tregear et al., Endocrinology, 93, 1349-1353 (1973)]; and vasopressin and a vasopressin derivative {refer to Desmopressin [Magazine of the Japan Endocrine Society, vol. 54, No. 5, pp. 676-691 (1978)]}.

Oxytocin, calcitonin, and a derivative having the same action as that of calcitonin, for example, a compound represented by the following formula (VI) or a salt thereof:

(VI)

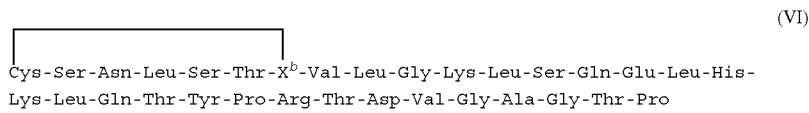

Cys-Ser-Asn-Leu-Ser-Thr-$X^b$-Val-Leu-Gly-Lys-Leu-Ser-Gln-Glu-Leu-His-
Lys-Leu-Gln-Thr-Tyr-Pro-Arg-Thr-Asp-Val-Gly-Ala-Gly-Thr-Pro

[wherein $X^b$ represents 2-aminosuberic acid] [refer to Endocrinology, 1992, 131/6 (2885-2890)]; glucagons; gastrin; secretin; cholecystokinin; and angiotensin.

Enkephalin and an enkephalin derivative, for example, an oligopeptide such as a peptide represented by the following formula (VII) or a salt thereof:

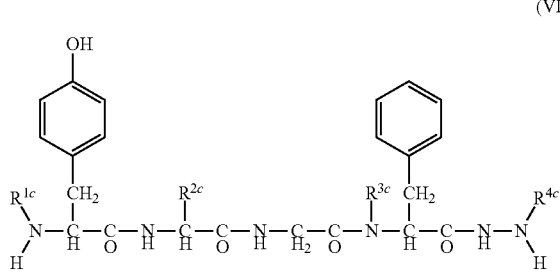

(VII)

[wherein each of $R^{1c}$ and $R^{3c}$ represents hydrogen or an alkyl group containing 1 to 6 carbon atoms; $R^{2c}$ represents hydrogen or a D-α-aminoacid; and $R^{4c}$ represents hydrogen or a substitutable aliphatic acyl group containing 1 to 8 carbon atoms] (refer to U.S. Pat. No. 4,277,394 and European Patent Application Laid-Open No. 31567), and endorphin.

Kyotorphin; interleukin (I to XI); tuftsin; thymopoietin; a thymic humoral factor (THF); and a serum thymic factor (FTS) and a derivative thereof, for example, a peptide represented by the following formula (VIII) or a salt thereof:

PGlu-Xd-Lys-Ser-Gln-Yd-Zd-Ser-Asn-OH       (VIII)

[wherein Xd represents L- or D-Ala; and each of Yd and Zd represents Gly or a D-amino acid containing 3 to 9 carbon atoms] (refer to U.S. Pat. No. 4,229,438); and other thymic hormones [refer to Thymosin α1 and β4, thymic factor X, and the like, Igaku no Ayumi (Progress of Medicine), vol. 125, No. 10, kpp. 835-843 (1983)].

Motilin; deinorphin; bombesin; neurotensin; caerulein; bradykinin; urokinase; substance P; polymyxin B; colistin; gramicidin; bacitracin; a protein synthesis stimulating peptide; (refer to G.B. Patent No. 8232082); a gastric-acid secretion inhibitory polypeptide (GIP); a vasoactive intestinal polypeptide (VIP)]; a platelet-derived growth factor (PDGF); and a growth hormone releasing factor (GRF, somatocrinin); and the like.

These bioactive peptides may be derived from either humans, or other animals such as a bovine, swine, chicken, red fish, or eel. Otherwise, such a bioactive peptide may be a chimeric body consisting of a human and such an animal. Moreover, an active derivative having a partially modified structure may also be used. For example, a peptide represented by the following formula (IX), which is insulin derived from swine, calcitonin derived from swine, chicken, red fish or eel, or a chimeric body consisting of a human and red fish:

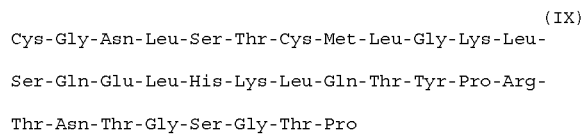

(IX)
Cys-Gly-Asn-Leu-Ser-Thr-Cys-Met-Leu-Gly-Lys-Leu-

Ser-Gln-Glu-Leu-His-Lys-Leu-Gln-Thr-Tyr-Pro-Arg-

Thr-Asn-Thr-Gly-Ser-Gly-Thr-Pro or the like is used (refer to [Endocrinology, 1992, 131/6 (2885-2890)].

Moreover, a drug for regulating the rate of dissolution of a drug, an additive drug used for stabilization, an adsorption inhibitor, and the like, may be added to the drug.

As an absorber, a material capable of favorably absorbing a liquid is selected. Examples of such an absorber may include polyester (polyethylene terephthalate), polysaccharides or cellulose derivatives (rayon, cotton), polyamide (nylon); non-woven fabric, woven fabric, gauze, or sponge thereof: or hydrophilic polymers (agar, agarose, alginic acid, xanthan gum, Cyamoposis gum, dextran, dextrin, Pullulan, chitosan, gelatin, a carboxyvinyl polymer, polyacrylate, a carboxymethyl cellulose salt, polyoxyalkylene, polyvinyl alcohol, polyvinylpyrrolidone, polyacrylamide), and ion exchange resins (amberlite, diaion, cholestyramine). A preferred example is a non-woven fabric having rayon as a main component.

As a wall material, a non-water-permeable material is selected. Examples of such a wall material may include polyolefin foam (PE, PP, etc.), polyurethane foam, polystyrene foam, foamed rubber (polybutylene, etc.), EVA foam, and PVC foam. A preferred example is polyolefin foam.

Examples of an adhesive layer may include natural rubber, astyrene-isoprene-styrene block copolymer, styrene-butadiene rubber, styrene-isoprene rubber, polyisobutyrene, polyisoprene, polyacrylate, and silicon rubber. A preferred example is polyacrylate.

As a support, a non-water-permeable material is selected. Example of such a support may include polyolefin foam (PE, PP, etc.), polyurethane foam, polystyrene foam, foamed rubber, EVA foam, and PVC foam. A preferred example is polyolefin foam.

Examples of a dissolution liquid reservoir may include: a molded sheet, which is produced by molding into a dome shape, a sheet material consisting of PET, PVC, PVDC, PP, PE, polystyrene, cyclic polyolefin (COC), Al, and a laminated body thereof, and then forming a convex protruding portion therein; sheets having high barrier properties (PCTFE/PP, PCTFE/PVC, cyclic polyolefin/PP); and Al-evaporated or $SiO_2$-evaporated sheets. When the convex protruding portion of the dissolution liquid reservoir is pressed, at least one selected from a diaphragm and a laminated body consisting of the diaphragm and a support is destroyed. If the convex protruding portion has a conical form, a portion to be destroyed thereby becomes a point, and thus, permeation of a dissolution liquid into the absorber side becomes poor. Accordingly, the form of the convex breaking portion (that is, the tip of the protruding portion) is preferably linear or planar. The material therefor may be either PCTFE $(—CF2-CFCl—)_n$ poly (chloro-trifluoroethylene), or a COC cyclic polyolefin copolymer. The thickness of the sheet is between 100 and 500 μm. As a dissolution liquid reservoir, PP, PP/COC/PP, or PCTFE/PP is preferably used, for example.

Examples of a diaphragm (film broken by a protruding portion) may include Al, Ti, Ag, PP, PE, and a laminated body thereof. An Al foil is preferably coated, so as to prevent it from corrosion, as necessary. The thickness of such a diaphragm is between 5 and 100 μm in the case of Al, and is between 15 and 50 μm in the case of PP or PE, for example.

Examples of a dissolution liquid may include water, alcohols, polyhydric alcohols, surfactants, sugars, pH regulators (organic and inorganic acids or bases), salts, water-soluble polymers, resolvents, absorbefacients, oils and fats, and preservatives. Of these, preferred examples may include water+polyhydric alcohol, purified water, glycerin, and methylparaben (propylparaben, propylene glycol).

Examples of a liner may include PET, PEN, PP, PE, a paper, Al, and a laminated body thereof. A preferred example is PET. In addition, it is preferable to perform a mold releasing surface treatment such as a silicon surface treatment. Moreover, a liner may be process in a concave form, so that it is not allowed to come into contact with a member that contains a drug.

Examples of a drying drug may include previously wrapped silicagel, Ca oxide, Ca chloride, Mg chloride, montmorillonite, and zeolite.

Examples of an electrode may include Ag, AgCl, Ti, and carbon. Of these, preferred examples may include Ag and AgCl. Such an electrode can be also used as a diaphragm. When an electrode is not used as a diaphragm, an opening is provided as in the case of a support. Such an opening is provided in one or more portions, and it has a diameter of 2 mm or greater.

Figure 2:
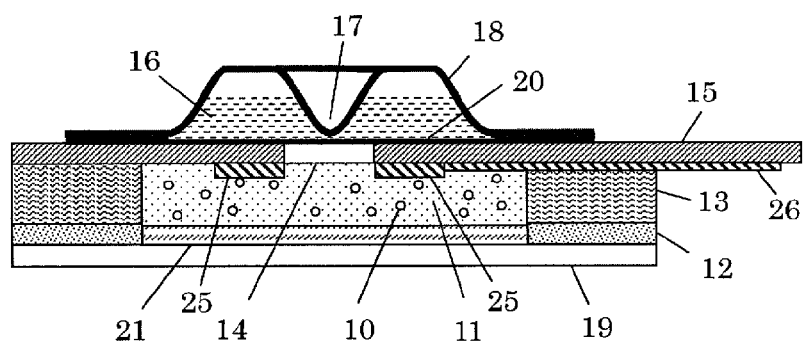
FIG. 2 is a cross-sectional view showing another structure example of the iontophoresis device activated in use of the present invention.

FIG. 2 is a cross-sectional view showing another structure example of the iontophoresis device activated in use of the present invention. The device of the present example differs from the device shown in FIG. 1, in that a solution permeable film 21 is provided on the undersurface of the absorber 11 that contains a drug. Other than this point, the device of the present example is the same as that shown in FIG. 1. The solution permeable film 21 is effective for retaining the absorber, and it is provided also as a retaining means when a powdery substance is contained.

Examples of a solution permeable film used herein may include a porous film and an ion exchange film. Examples of such a porous film may include PE, PP, cellulose, cellulose acetate, PET, and nylon. Examples of such an ion exchange film may include a cation exchange film, an anion exchange film, and a complex charged film. A nylon cation exchange film is preferably used. However, when the absorber is a non-woven fabric, a solution permeable film is unnecessary.

Figure 3:
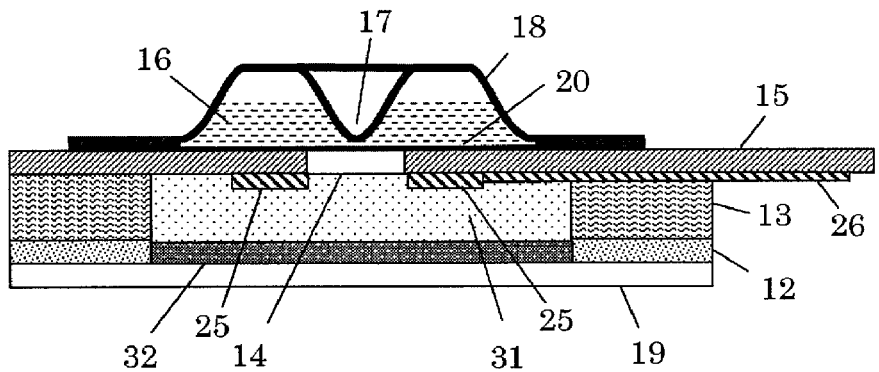
FIG. 3 is a cross-sectional view showing another structure example of the iontophoresis device activated in use of the present invention.

FIG. 3 is a cross-sectional view showing another structure example of the iontophoresis device activated in use of the present invention. In the device of the present example, the absorber 11 that contains a drug shown in FIG. 1 is divided into two portions, namely, an absorber 31 that does not contain a drug and a drug-containing layer 32. The structure other than this is the same as that shown in FIG. 1. The reason why the absorber is divided into the absorber 31 and the drug-containing layer 32 is that the drug is allowed to come into contact with a living body at a high concentration, so as to exert the absorption of the drug to the maximum.

As a drug-containing layer, a porous film or ion exchange film that contains a drug can be used, for example. Examples of a porous film may include PE, PP, cellulose, cellulose acetate, PET, and nylon. Examples of an ion exchange film may include a cation exchange film, an anion exchange film, and a complex charged film. A nylon cation exchange film is preferably used.

Figure 4:
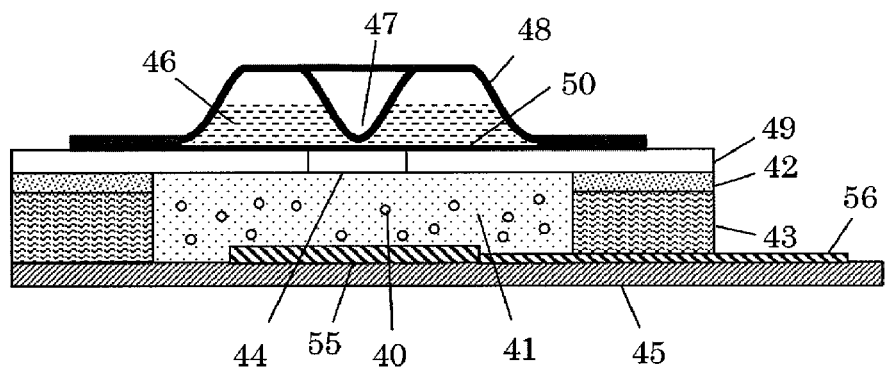
FIG. 4 is a cross-sectional view showing another structure example of the iontophoresis device activated in use of the present invention.

FIG. 4 is a cross-sectional view showing another structure example of the iontophoresis device activated in use of the present invention. The device of the present example differs from the aforementioned devices shown in FIGS. 1 to 3, in that a dissolution liquid reservoir is removed when the device is used. As shown in the figure, the device of the present example comprises: a support 45; an electrode 55 disposed on the upper surface of the support 45; an absorber 41, which is disposed on the support 45 and the electrode 55 and is formed of a material containing a dry drug 40 and capable of absorbing a liquid; a wall material 43, which is disposed around the absorber 41 on the support 45 and has an adhesive layer 42 on the upper surface thereof; a liner 49, which is disposed on the absorber 41 and the adhesive layer 42 and has an opening 44 in the central portion thereof; a diaphragm 50 disposed on the liner 49; and a dissolution liquid reservoir 48, which is disposed on the diaphragm 50, retains a dissolution liquid for dissolving the drug between the diaphragm 50 and itself, and has a protruding portion 47 for destroying the diaphragm 50 by pressing force. The protruding portion 47 is configured in the same manner as that shown in FIG. 1. The liner 49 is removably attached to the adhesive layer 42. The form and size of the opening 44 of the liner are the same as those in the case of FIG. 1.

When the above device is used, first, the upper surface of the dissolution liquid reservoir 48 is pressed, so that the protruding portion 47 breaks the diaphragm 50. At this time, the diaphragm 50 is broken as a result of the pressure from the protruding portion 47, and a dissolution liquid contained therein is then supplied to the absorber 41 via the opening 44 of the liner 49. The absorber 41 gets wet with this dissolution liquid, and the drug 40 is thereby evenly activated. Thereafter, the liner 49 is removed together with the dissolution liquid 48, and the present device is then attached to the skin. As in the case of FIG. 1, by actuating a power supply used for iontophoresis, an electric voltage or current is supplied to a portion between the present iontophoresis device and a counter device. Thereby, the activated drug permeates into the skin. In the present example, since the dissolution liquid 48 and the liner 49 are removed from the main body of the device when it is used, it is preferable that the device be attached after the dissolution liquid contained in the dissolution liquid reservoir 48 has become empty.

Figure 5:
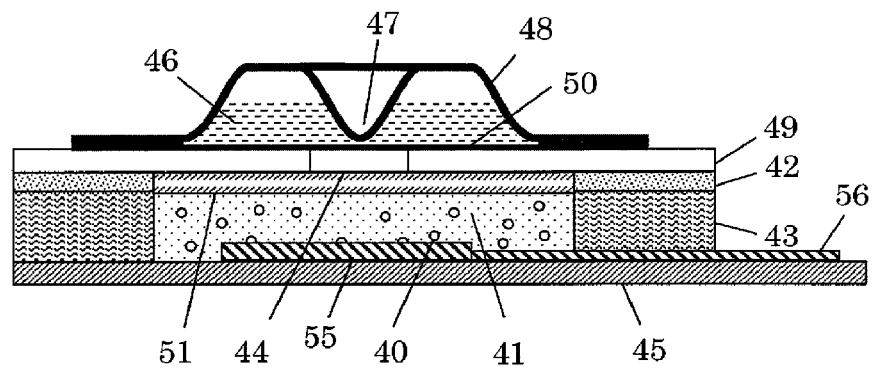
FIG. 5 is a cross-sectional view showing another structure example of the iontophoresis device activated in use of the present invention.

FIG. 5 is a cross-sectional view showing another structure example of the iontophoresis device activated in use of the present invention. The device of the present example differs from the device shown in FIG. 4, in that a solution permeable film 51 is provided on the upper surface of the absorber 41 that contains a drug. Except for this point, the device of the present example is the same as that shown in FIG. 4. Herein, the reason why the solution permeable film 51 is provided and the material therefor are the same as those described in FIG. 2 above.

Figure 6:
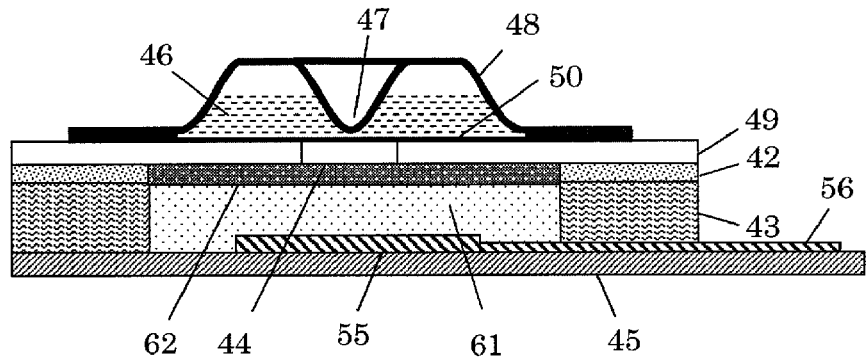
FIG. 6 is a cross-sectional view showing another structure example of the iontophoresis device activated in use of the present invention.

FIG. 6 is a cross-sectional view showing another structure example of the iontophoresis device activated in use of the present invention. In the device of the present example, the absorber 41 that contains a drug shown in FIG. 4 is divided into two portions, namely, an absorber 61 that does not contain a drug and a drug-containing layer 62. Except for this point, the device of the present example is the same as that shown in FIG. 4. The reason why the absorber 41 is divided into the absorber 61 and the drug-containing layer 62 and the material therefor are the same as those described in FIG. 3 above.

Figure 7:
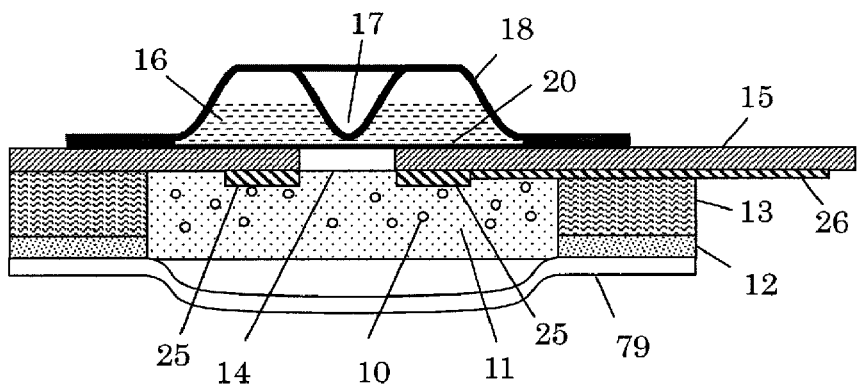
FIG. 7 is a cross-sectional view showing a further structure example of the iontophoresis device activated in use of the present invention.

FIG. 7 is a cross-sectional view showing a further structure example of the iontophoresis device activated in use of the present invention. The device of the present example differs from the device shown in FIG. 1, in that a liner 79 is provided on the undersurface of both the absorber and the adhesive layer, wherein the liner has a concave portion opposed to the above described absorber. Except for this point, the device of the present example is the same as that shown in FIG. 1. Herein, the liner 79 is processed into a concave form because it is not allowed to come into contact with a member that contains a drug.

Figure 8:
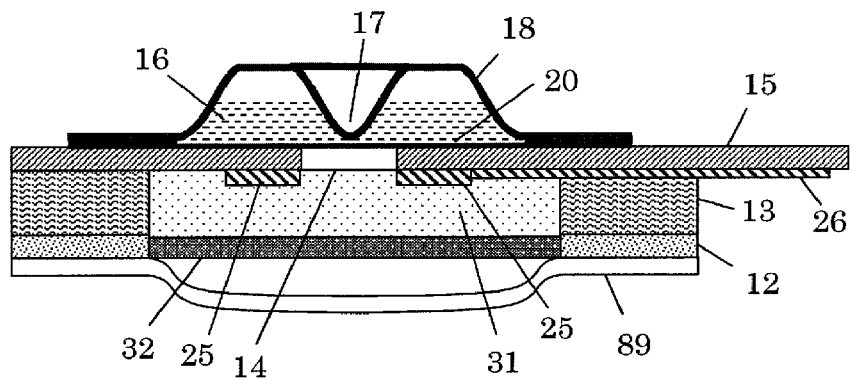
FIG. 8 is a cross-sectional view showing a further structure example of the iontophoresis device activated in use of the present invention.

FIG. 8 is a cross-sectional view showing a further structure example of the iontophoresis device activated in use of the present invention. The device of the present example differs from the device shown in FIG. 3, in that a liner 89 is provided on the undersurface of both the drug-containing layer and the adhesive layer, wherein the portion thereof opposed to the above described drug-containing layer has a concave form. Except for this point, the device of the present example is the same as that shown in FIG. 3. Herein, the liner 89 is processed into a concave form because it is not allowed to come into contact with a member that contains a drug.

Figure 9:
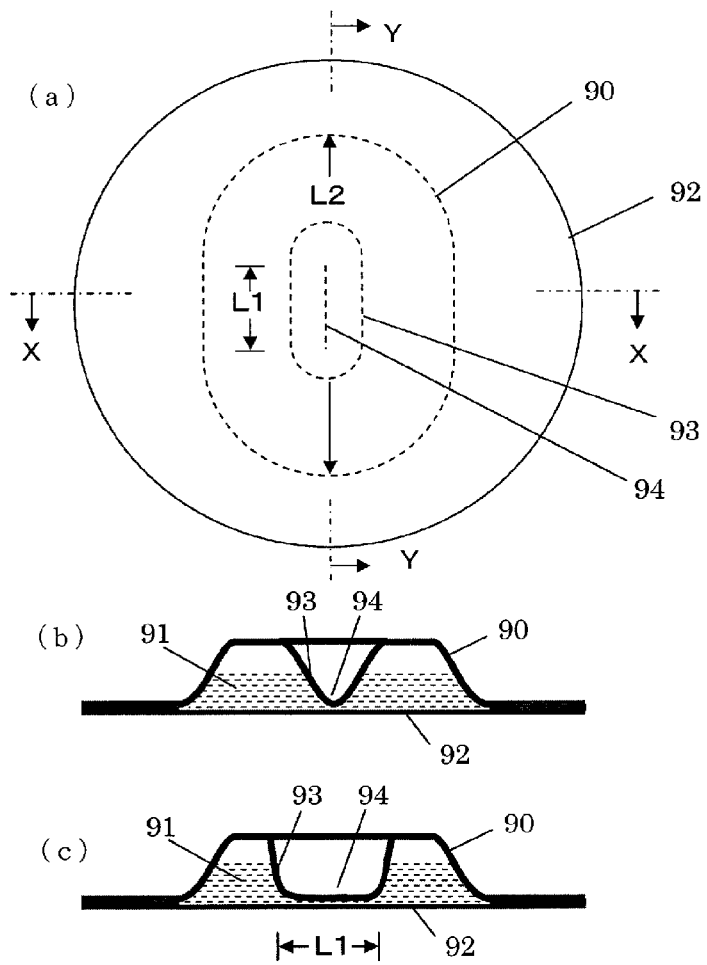
FIG. 9 is a view showing a structure example of a dissolution liquid reservoir used in the iontophoresis device activated in use of the present invention, wherein (a) represents a plan view, (b) represents a cross-sectional view of (a) along the line X-X, and (c) represents a cross-sectional view of (a) along the line Y-Y.

FIG. 9 is a view showing a structure example of a dissolution liquid reservoir used in the iontophoresis device activated in use of the present invention, wherein (a) represents a plan view, (b) represents a cross-sectional view of (a) along the line X-X, and (c) represents a cross-sectional view of (a) along the line Y-Y. In the present example, the configuration is devised such that a dissolution liquid contained in the dissolution liquid reservoir is supplied to the absorber in an as large as possible amount, when it is used. A dissolution liquid reservoir 90 of the present example retains a dissolution liquid 91 and comprises a protruding portion 93 for breaking a diaphragm 92 by pressing force when it is used. As shown in the figure, the dissolution liquid-contacting portion of the diaphragm 92 of the present example has an oval form, and the diaphragm 92 itself has a round form. The protruding portion 93 has a linear apical portion 94 that extends in the longitudinal direction of the oval form of the dissolution liquid-contacting portion of the diaphragm 92. When the length of the linear apical portion 94 is given by L1 and the length of the dissolution liquid-contacting portion of the diaphragm 92 in the longitudinal direction is given by L2, the present device is designed such that it satisfies such a relationship as $0.1 \times L2 \leq L1 \leq 0.5 \times L2$. Thereby, for the use of the present device, when the protruding portion 93 is pressed, the diaphragm 92 is significantly broken along the liner apical portion 94, and the dissolution liquid 91 is then favorably flown to the outside, so that the amount of a liquid remaining in the reservoir can be reduced. In the present example, the linear apical portion 94 is disposed separately from the diaphragm 92. However, it may also be possible that the two components be allowed to come into contact with each other.

Figure 10:
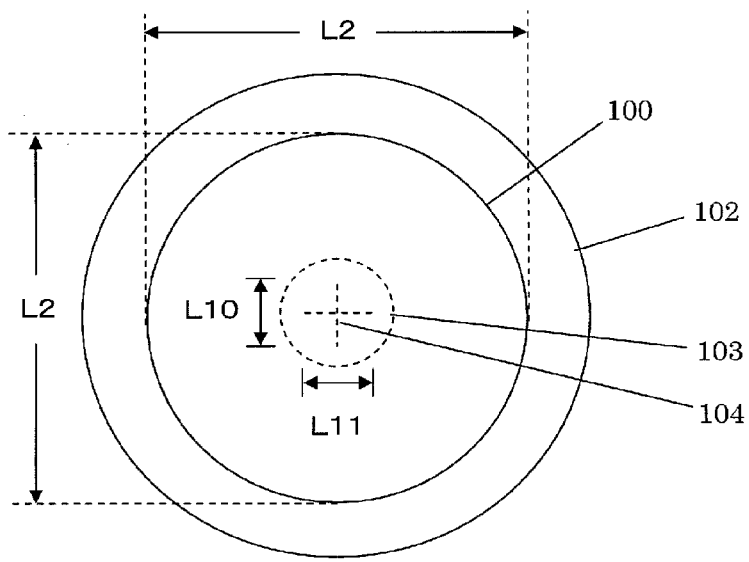
FIG. 10 is a plan view showing another structure example of a dissolution liquid reservoir used in the iontophoresis device activated in use of the present invention.

FIG. 10 is a plan view showing another structure example of a dissolution liquid reservoir used in the iontophoresis device activated in use of the present invention. A dissolution liquid reservoir 100 of the present example particularly differs from the reservoir shown in FIG. 9, in that the dissolution liquid-contacting portion of a diaphragm 102 of the present example has a round form, as with the diaphragm 102, and also in that a protruding portion 103 has cross-shape apical portions 104. When the lengths of the cross-shape apical portions 104 are given by L10 and L11 and the diameter of the dissolution liquid-contacting portion of the diaphragm 102 is given by L2, the present device is designed such that it satisfies such relationships as $0.1 \times L2 \leq L10 \leq 0.5 \times L2$ and/or $0.1 \times L2 \leq L11 \leq 0.5 \times L2$. Thereby, for the use of the present device, when the protruding portion 103 is pressed, the diaphragm 102 is significantly broken by the cross-shape apical portions 104, and the dissolution liquid is then favorably flown to the outside, so that the amount of a liquid remaining in the reservoir can be reduced.

Figure 11:
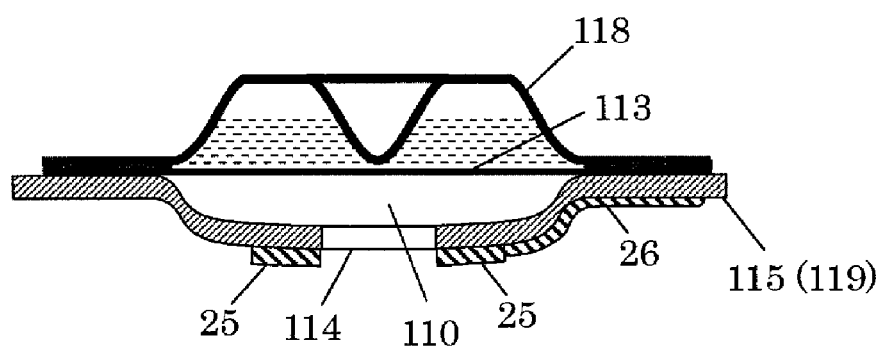
FIG. 11 is a cross-sectional view showing a structure example of a support or liner used in the present invention.

FIG. 11 is a cross-sectional view showing a structure example of a support or liner of the present invention. In the present example, the configuration is devised such that a dissolution liquid contained in the dissolution liquid reservoir is rapidly supplied to the absorber when it is used. Such configuration can be applied to the support in the structure examples shown in FIGS. 1 to 3, 7, and 8, and can be applied to the liner in the structure examples shown in FIGS. 4 to 6. As shown in the figure, the portion around an opening 114 for feeding a dissolution liquid of a support 115 or a liner 119 of the present example is dented to the absorber side, rather than other portions, namely, to the side opposite to a dissolution liquid 118. Thereby, a space 110 is formed in a portion between the support 115 or liner 119 and the dissolution liquid reservoir 118. For the use of the present device, when the dissolution liquid reservoir 118 is pressed, the diaphragm 113 is broken. A portion of the thus broken diaphragm spreads out into the space 110, so that a dissolution liquid can be rapidly flown to the opening 114 and so that the amount of a liquid remaining in the reservoir can be reduced.

Figure 12:
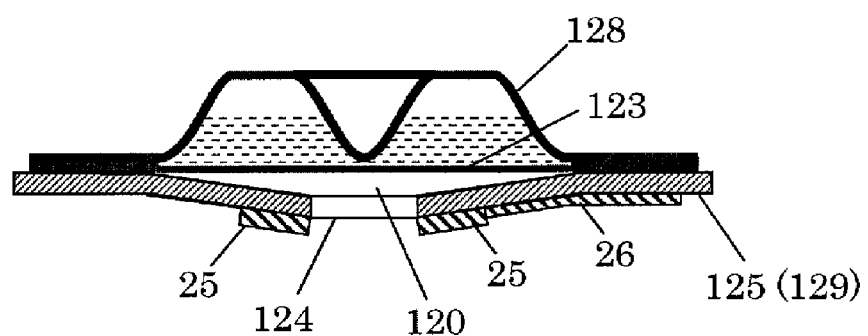
FIG. 12 is a cross-sectional view showing another structure example of a support or liner used in the present invention.

FIG. 12 is a cross-sectional view showing another structure example of a support or liner of the present invention. In the present example as well, the configuration is devised such that a dissolution liquid contained in the dissolution liquid reservoir is rapidly supplied to the absorber when it is used. Such configuration can be applied to the support in the structure examples shown in FIGS. 1 to 3, 7, and 8, and can be applied to the liner in the structure examples shown in FIGS. 4 to 6. As shown in the figure, the portion ranging from the peripheral portion to an opening 124 of a support 125 or a liner 129 of the present example is inclined toward the absorber side. In this case also, a space 120 is formed in a portion between the support 125 or liner 129 and a dissolution liquid reservoir 128. For the use of the present device, when the dissolution liquid reservoir 128 is pressed, a diaphragm 123 is broken. A dissolution liquid can be rapidly flown to the opening 124 without spreading out to the peripheral portion, and the amount of a liquid remaining in the reservoir can be reduced.

A dissolution liquid container is formed by the combination of a dissolution liquid reservoir with a diaphragm. Hereafter, a preferred structure example of such a dissolution liquid container will be described. The dissolution liquid container comprises a dissolution liquid reservoir, in at least a portion of which a protruding portion has been formed. This protruding portion can be formed by molding processing. A strength is controlled such that it is capable of breaking the diaphragm when the protruding portion is pressed. Accordingly, a sheet material (film) containing aluminum is likely to generate crack or breakage, and thus it is not suitable for processing into a protruding portion.

In the present invention, a sheet material (film) used for a dissolution liquid container (dissolution liquid reservoir) has a water vapor permeability of 0.30 $g/m^2 \cdot 24$ hr or less, and more preferably 0.22 $g/m^2 \cdot 24$ hr or less, for example. An example of such a sheet material is a film comprising a cyclic polyolefin copolymer (COC) or a fluorocarbon resin. A preferred example is a fluorocarbon resin laminated film. Moreover, with regard to the inner surface of the container, since the possibility of heat-sealing with a diaphragm results in excellent sealing performance, a fluorocarbon resin film is preferably laminated with a polyvinyl chloride (PVC), polypropylene (PP), or polyethylene (PE) film. Furthermore, from the viewpoint of drug-absorbing ability, a laminated film formed by the combination of such films with a polypropylene or polyethylene film is more preferable. From the viewpoint of breaking ability and processability, the thickness of a sheet material (film) is thinner than approximately 500 μm, preferably between approximately 100 and 400 μm, and more preferably between approximately 250 and 350 μm. As a diaphragm, an aluminum foil is preferable.

EXAMPLES

Production of Dissolution Liquid Container:

For example, the dissolution liquid reservoir having a protruding portion shown in FIG. 3 was produced by molding processing. Thereafter, a dissolution liquid (600 μl of a 30 w/w % glycerin aqueous solution) was placed in this dissolution liquid reservoir, and a processed aluminum foil (20 μm), on which an acryl adhesive material (DURO-TAK 87-2516, 50 μm) had been laminated, was heat-sealed to the above reservoir (140° C. to 150° C., 2 seconds), thereby producing a dissolution liquid container.

Production of Dissolution Liquid-Integrated Patch:

The acryl adhesive face of the thus produced dissolution liquid container was attached to the top portion of a formulation, so as to produce a formulation as shown in FIG. 3, for example.

Production of Alprostadil-Containing Dissolution Liquid-Integrated Patch:

The acryl adhesive face of the thus produced dissolution liquid container was attached to the top portion of a formulation, so as to impregnate the drug-containing layer of a formulation as shown in FIG. 3, for example, with a drug (5 mg of alprostadil alfadex) and 8 mg of lactose, thereby producing a formulation. The produced formulation was conserved together with a drying drug (1 g of Tri-sorb, Sud-Chemie) in an aluminum wrapping material.

Examples and comparative examples are given below.

Example 1

The material used for a dissolution liquid container (dissolution liquid reservoir) is a laminated body (PE/COC/PE) consisting of a PE film, a COC film, and a PE film. The material has a thickness of 350 μm and a water vapor permeability of 0.22 g/m$^2$·24 hr.

Example 2

The material used for a dissolution liquid container (dissolution liquid reservoir) is a laminated body (PP/PCTFE) consisting of a PP film and a PCTFE (fluorocarbon resin) film. The material has a thickness of 300 μm and a water vapor permeability of 0.11 g/m$^2$·24 hr.

Example 3

The material used for a dissolution liquid container (dissolution liquid reservoir) is a laminated body (PP/PCTFE) consisting of a PP film and a PCTFE (fluorocarbon resin) film. The material has a thickness of 250 μm and a water vapor permeability of 0.14 g/m$^2$·24 hr.

Comparative Example 1

The material used for a dissolution liquid container (dissolution liquid reservoir) is a PVC film. The material has a thickness of 300 μm and a water vapor permeability of 2.70 g/m$^2$·24 hr.

Comparative Example 2

The material used for a dissolution liquid container (dissolution liquid reservoir) is a PP film. The material has a thickness of 300 μm and a water vapor permeability of 0.70 g/m$^2$·24 hr.

Comparative Example 3

The material used for a dissolution liquid container (dissolution liquid reservoir) is a PP film. The material has a thickness of 500 μm and a water vapor permeability of 0.32 g/m$^2$·24 hr.

Comparative Example 4

The material used for a dissolution liquid container (dissolution liquid reservoir) is a laminated body (PE/COC/PE) consisting of a PE film, a COC film, and a PE film. The material has a thickness of 500 μm and a water vapor permeability of 0.14 g/m$^2$·24 hr.

Comparative Example 5

The material used for a dissolution liquid container (dissolution liquid reservoir) is a laminated body (Al/PP) consisting of an Al film and a PP film. The material has a thickness of 150 μm and a water vapor permeability of 0 g/m$^2$·24 hr.

With regard to each of the aforementioned examples and comparative examples, the processability and diaphragm-breaking ability of the protruding portion of each dissolution liquid container were evaluated. The results shown in Table 1 were obtained.

TABLE 1

| | Material and properties of container | | | | |
|---|---|---|---|---|---|
| | Material of container | Thickness (μm) | Water vapor permeability (g/m$^2$) | Processability of protruding portion | Diaphragm-breaking ability |
| Com. Ex. 1 | PVC | 300 | 2.70 | ◯ | ◯ |
| Com. Ex. 2 | PP | 300 | 0.70 | ◯ | ◯ |
| Com. Ex. 3 | PP | 500 | 0.32 | ◯ | x |
| Com. Ex. 4 | PE/COC/PE | 500 | 0.14 | ◯ | x |
| Com. Ex. 5 | Al/PP | 150 | 0 | x | ◯ |
| Ex. 1 | PE/COC/PE | 350 | 0.22 | ◯ | ◯ |
| Ex. 2 | PP/PCTFE | 300 | 0.11 | ◯ | ◯ |
| Ex. 3 | PP/PCTFE | 250 | 0.14 | ◯ | ◯ |

Water vapor permeability: 40° C., 90% RH, 24 hr (24 hours)

As shown in Table 1, with regard to Examples 1 to 3 and Comparative examples 1 and 2, both the processability and diaphragm-breaking ability of the protruding portion were favorable (O). With regard to Comparative examples 3 and 4 (a film thickness of approximately 500 μm), the processability of the protruding portion was favorable (O). However, the strength of the dissolution liquid container was too high, and thus the diaphragm-breaking ability of the protruding portion was extremely decreased (x). With regard to Comparative example 5, the breakage of aluminum was observed during the processing of the protruding portion, and the processability of the protruding portion was thereby poor (x).

Subsequently, a change in the weight of a dissolution liquid container and dissolution liquid migration were evaluated under each temperature condition. A dissolution liquid-integrated patch was produced, and the patch was then conserved at temperatures of 40° C. and 50° C. for 1 month. Thereafter, a reduction in the amount of the dissolution liquid (vs. initial %) and the migration of the dissolution liquid were evaluated. The results shown in Table 2 were obtained. With regard to the migration of the dissolution liquid, a case where the time at which the transition of the solution to the entire surface of a drug-retaining film was observed after the dissolution liquid container had been pressed was shorter than approximately 30 seconds was defined as O, and a case where the above time was approximately 30 seconds or longer was defined as x.

TABLE 2

Change in weight of dissolution liquid container and dissolution liquid migration under each temperature condition

|  | | 40° C., 1 month | | 50° C., 1 month | |
| --- | --- | --- | --- | --- | --- |
|  | Material of container | Loss of dissolution liquid | Dissolution liquid migration | Loss of dissolution liquid | Dissolution liquid migration |
| Com. Ex. 1 | PVC | 15.3% | o | 27.6% | x |
| Com. Ex. 2 | PP | 5.9% | o | 14.1% | o |
| Ex. 1 | PE/COC/PE | 2.0% | o | 5.6% | o |
| Ex. 2 | PP/PCTFE | 0.3% | o | 1.0% | o |

A reduction in the amount of a dissolution liquid suitable for a long-term conservation is preferably 13% or less. In Examples 1 and 2, such a reduction in the amount of a dissolution liquid is 13% or less at temperatures of 40° C. and 50° C., and thus the containers of Examples 1 and 2 are suitable for a long-term conservation. On the other hand, in Comparative example 1, a significant reduction of the amount of the conserved dissolution liquid was observed at temperatures of 40° C. and 50° C., and in Comparative example 2, a significant reduction of the amount of the conserved dissolution liquid was observed at a temperature of 50° C. Accordingly, these containers are not suitable for a long-term conservation. In addition, the time required for the transition of the dissolution liquid to a drug-retaining film when it is activated for use is short in Examples 1 and 2 and Comparative example 2. However, in Comparative example 1, it took a long time for the transition of the dissolution liquid.

Taking into consideration the results shown in Tables 1 and 2, as described in Examples 1 to 3, a sheet material (film) used as a dissolution liquid container (dissolution liquid reservoir) preferably has a water vapor permeability of 0.22 g/m$^2$·24 hr or less. Moreover, such a sheet material preferably has a thickness between approximately 250 and approximately 350 μm. Such a sheet material comprises a cyclic polyolefin copolymer (COC) film or a fluorocarbon resin film. Such a sheet material is preferably a laminated film consisting of a cyclic polyolefin copolymer film and a polyolefin film, or a laminated film consisting of a fluorocarbon resin film and a polyolefin film.

INDUSTRIAL APPLICABILITY

The present invention can be applied to an iontophoresis device used in the medical field. The iontophoresis device activated in use of the present invention having a dissolution liquid reservoir is an iontophoresis device, which maintains the stability of a drug, is excellent in terms of versatility and practicability, and can easily be used. In addition, since this iontophoresis device activated in use enables reduction in the amount of a liquid remaining in a dissolution liquid reservoir when it is used, the concentration of a drug contained in the device can be maintained in accordance with provisions.

The invention claimed is:

1. An iontophoresis device activated in use comprising: a drug-containing layer containing a dry drug; an absorber disposed on said drug-containing layer and formed of a material capable of absorbing a liquid; a wall material disposed around said absorber, having an adhesive layer on the undersurface thereof; a support disposed on said absorber and said wall material, having an opening in the central portion thereof; an electrode disposed on the undersurface of said support; a diaphragm disposed on said support; and a dissolution liquid reservoir disposed on said diaphragm, retaining a dissolution liquid for dissolving said drug between said diaphragm and itself, and having a protruding portion for destroying said diaphragm by pressing force,
   wherein said dissolution liquid reservoir is formed by processing of a sheet material, said protruding portion being formed by molding processing in at least a portion of said dissolution liquid reservoir,
   wherein said sheet material is a laminated film consisting of a cyclic polyolefin copolymer film and a polyolefin film, or a laminated film consisting of a fluorocarbon resin film and a polyolefin film, and
   wherein said sheet material has a water vapor permeability of 0.22 g/m$^2$·24 hr or less and has a thickness between about 250 and about 350 μm.

2. The iontophoresis device activated in use according to claim 1, further comprising a liner on the undersurface of both said drug-containing layer and said adhesive layer, wherein said liner has a concave portion opposed to said drug-containing layer.

3. The iontophoresis device activated in use according to claim 1, wherein the dissolution liquid-contacting portion of said diaphragm has an oval form, and that the protruding portion of said dissolution liquid reservoir has a linear apical portion that extends in the longitudinal direction of said oval form.

4. The iontophoresis device activated in use according to claim 3, wherein assuming that the length of said linear apical portion is given by L1 and the length of the dissolution liquid-contacting portion of said diaphragm in the longitudinal direction is given by L2, the relationship of 0.1× L2≦L1≦0.5×L2 is satisfied.

5. The iontophoresis device activated in use according to claim 1, wherein the dissolution liquid-contacting portion of said diaphragm has a round form, and that the protruding portion of said dissolution liquid reservoir has cross-shape apical portions.

6. The iontophoresis device activated in use according to claim 4, wherein assuming that the lengths of said cross-shape apical portions are given by L10 and L11 and the diameter of the dissolution liquid-contacting portion of said diaphragm is given by L2, the relationships of $0.1 \times L2 \leq L10 \leq 0.5 \times L2$ and/or $0.1 \times L2 \leq L11 \leq 0.5 \times L2$ are satisfied.

7. The iontophoresis device activated in use according to claim 1, wherein the peripheral portion of the opening of said support is dented to said absorber side more than the rest of said support.

8. The iontophoresis device activated in use according to claim 1, wherein said support is inclined so that the opening is closer toward said absorber side than the peripheral portion of said support.

9. The iontophoresis device activated in use according to claim 1, wherein said sheet material comprises a cyclic polyolefin copolymer film.

10. The iontophoresis device activated in use according to claim 1, wherein said sheet material is a laminated film consisting of a cyclic polyolefin copolymer film and a polyolefin film.

11. The iontophoresis device activated in use according to claim 1, wherein said sheet material is a laminated film consisting of a fluorocarbon resin film and a polyolefin film.

12. The iontophoresis device activated in use according to claim 1, wherein said diaphragm is an aluminum foil.

* * * * *